United States Patent
Koutrouvelis

[11] Patent Number: 5,868,757
[45] Date of Patent: Feb. 9, 1999

[54] METHOD AND APPARATUS FOR INTERSTITIAL RADIATION OF THE PROSTATE GLAND

[75] Inventor: Panos G. Koutrouvelis, McLean, Va.

[73] Assignee: PGK, Enterprises, Inc., McLean, Va.

[21] Appl. No.: 852,156

[22] Filed: May 6, 1997

Related U.S. Application Data

[63] Continuation-in-part of Ser. No. 340,288, Nov. 16, 1994, Pat. No. 5,626,829.

[51] Int. Cl.[6] .............................. A61B 19/00; A61F 11/00
[52] U.S. Cl. .................. 606/130; 606/108; 424/1.11; 424/1.33
[58] Field of Search .................................. 606/130, 108; 424/1.11, 1.33

[56] References Cited

PUBLICATIONS

Medline 94108754 (1993).
Medline 92302534 (1992).

*Primary Examiner*—Paul J. Killos
*Attorney, Agent, or Firm*—Rosenthal & Osha LLP

[57] ABSTRACT

An apparatus for use with an imaging device in treatment of a medical condition of a patient, including an upright support member; a span supported by and adjustable relative to the upright support member; a protractor disposed on the span; and a needle guide supported by the protractor, the needle guide being adjustable in three dimensions to allow alignment with an image plane of the imaging device and to allow fixation of the needle guide at a desired position and angle adjacent the patient; wherein at least a portion of the stereotactic assembly including the needle guide is movable into and out of the imaging device with the patient while the needle guide is fixed in the desired position adjacent the patient.

14 Claims, 5 Drawing Sheets

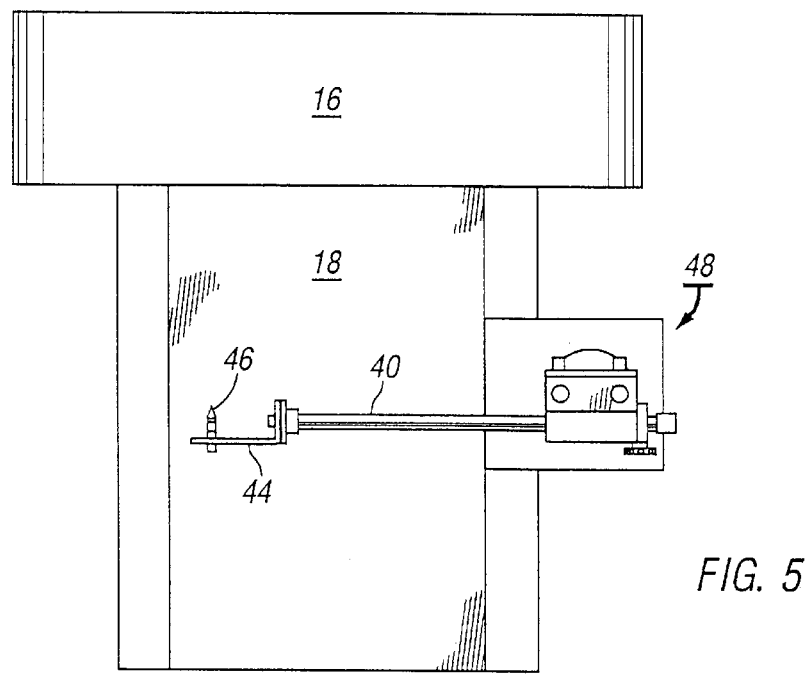
FIG. 5
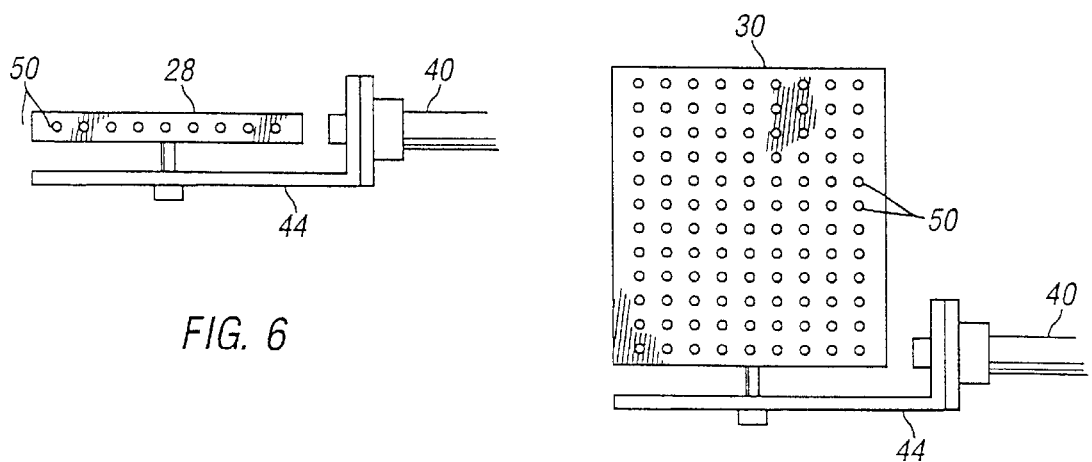
FIG. 6
FIG. 7

METHOD AND APPARATUS FOR INTERSTITIAL RADIATION OF THE PROSTATE GLAND

This is a continuation in part application of U.S. Application Ser. No. 08/340,288, filed on Nov. 16, 1994, now U.S. Pat. No. 5,626,829.

TECHNICAL FIELD OF THE INVENTION

The present invention relates to apparatus and method for the treatment of prostate cancer and, in particular, to an apparatus and method for prostate brachytherapy.

BACKGROUND OF THE INVENTION

Prostatic cancer has been estimated to affect as many as one in three men. In the U.S. alone, this implies an estimated fifty-million patients who are candidates for treatment of prostatic cancer. Prior methods of treatment include surgical intervention, external radiotherapy, and brachytherapy (interstitial radiation). A general discussion of the localized use of radiation therapy is found in Bagshaw, M. A., Kaplan, I. D. and Cox, R. C., Radiation Therapy for Localized Disease, CANCER 71:939–952, 1993. Disadvantages associated with surgical intervention include impotence and incontinence. External radiotherapy may have deleterious effects on surrounding normal tissues (e.g., the bladder, the rectum, and the urethra). In contrast, brachytherapy diminishes complications such as impotence and incontinence, and allows a higher and more concentrated radiation dose to be delivered to the prostate gland as compared to external radiotherapy. An additional advantage of brachytherapy is that treatment can be accomplished within a matter of days as compared to weeks, greatly reducing radiation exposure of the adjacent organs.

Prostate brachytherapy can be divided based upon the radiation level used into temporary implantation, which uses high activity sources, and permanent implantation, which uses lower activity sources. These techniques are described in Porter, A. T. and Forman, J. D., Prostate Brachytherapy, CANCER 71:953–958, 1993. The predominant radioactive sources used in prostate brachytherapy include iodine-125, palladium-103, gold-198, ytterbium-169, and iridium-192. Prostate brachytherapy can also be categorized based upon the method by which the radioactive material is introduced into the prostate. For example, an open or closed procedure can be performed via a suprapubic or a perineal retropubic approach.

SUMMARY OF THE INVENTION

In one aspect, this invention relates to an apparatus for use with an imaging device in treatment of a medical condition of a patient, including an upright support member; a span supported by and adjustable relative to the upright support member; a protractor disposed on the span; and a needle guide supported by the protractor, the needle guide being adjustable in three dimensions to allow alignment with an image plane of the imaging device and to allow fixation of the needle guide at a desired position and angle adjacent the patient; wherein at least a portion of the stereotactic assembly including the needle guide is movable into and out of the imaging device with the patient while the needle guide is fixed in the desired position adjacent the patient.

BRIEF DESCRIPTION OF THE DRAWINGS

FIG. 5 is a top view of a table mounted stereotactic device assembly according to an embodiment of FIG. 4.

FIG. 6 is a top view of a template mounted on a stereotactic device according to an embodiment of the invention.

FIG. 7 is a top view of a template mounted on a stereotactic device according to another embodiment of the invention.

DESCRIPTION OF THE PREFERRED EMBODIMENTS

Preferred embodiments of the invention will now be described with reference to the accompanying figures.

Although transperineal interstitial implantation of the prostate has been widely used, the transgluteal technique for brachytherapy of the prostate provides significant advantages. For example, the transgluteal technique does not require hospitalization or use of an operating room (i.e., may be performed on an out-patient basis). Moreover, transgluteal brachytherapy may be performed under local rather than general or spinal anesthesia. This feature significantly reduces recovery time following the procedure. From an anatomical perspective, transgluteal brachytherapy reduces the risk of prostatic urethra puncture, eliminates interference from skeletal structures during needle insertion, and reduces the need for cystoscopy. All of these factors combine to reduce procedural risk as compared to traditional methods of treating prostate cancer.

In addition to the general advantages of transgluteal brachytherapy, the method of the present invention enhances the accuracy of radioactive seed placement by combining computer aided tomography and a 3-D stereotactic system for precise transgluteal insertion of the seeds in the prostate gland. In addition, verification of needle position prior to and after seed implantation further improves seed placement.

Figure 1:
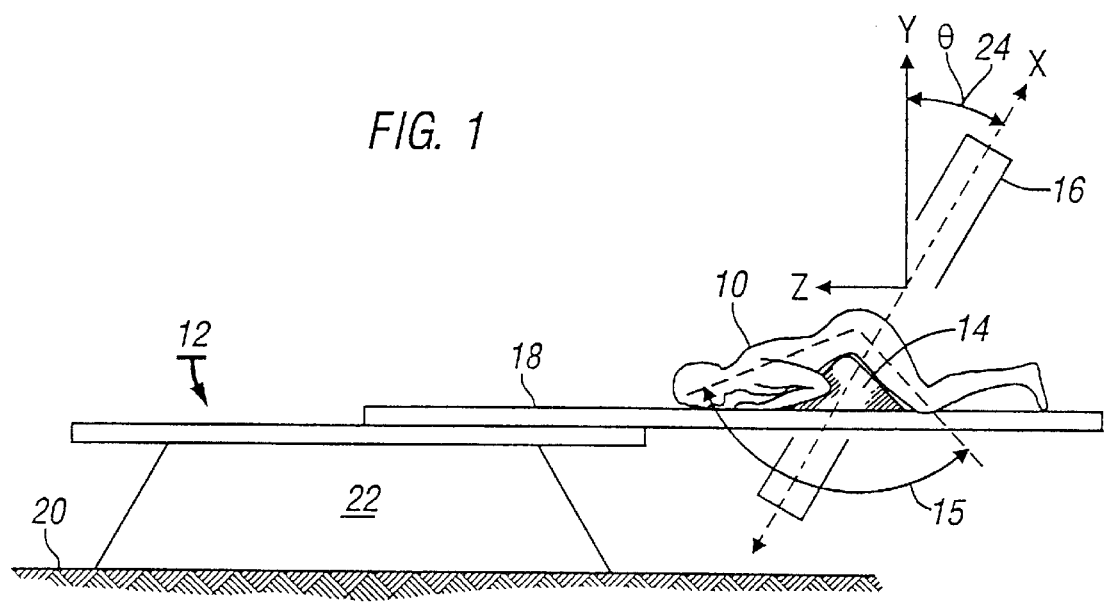
FIG. 1 is a side view of a patient positioned for transgluteal prostate brachytheraphy according to an embodiment of the invention.
Figure 2:
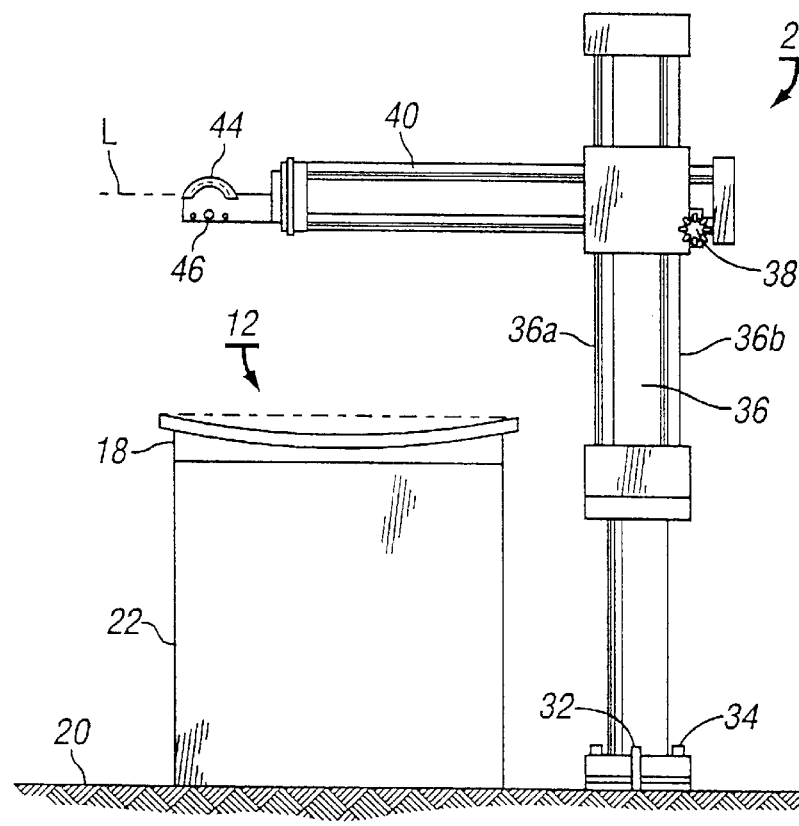
FIG. 2 is an end view of a floor mounted stereotactic device assembly according to an embodiment of the invention.
Figure 3:
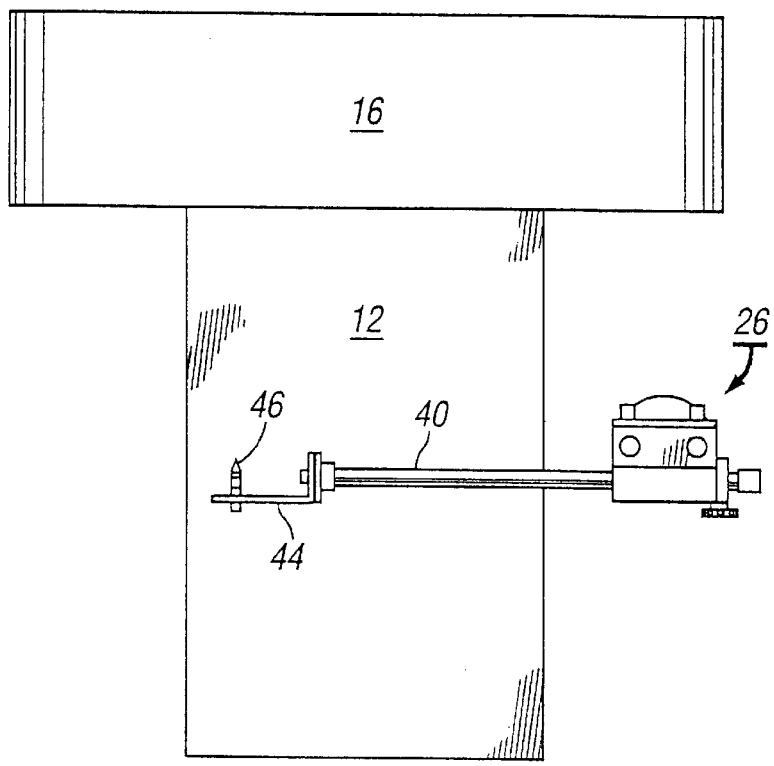
FIG. 3 is a top view of a floor mounted stereotactic device assembly according to an embodiment of FIG. 2.

The brachytherapy method of the present invention (See FIG. 1) includes identifying a patient in need of treatment for prostate carcinoma. A metastatic work-up is then performed including computer-aided tomography (CAT) or magnetic resonance imaging (MRI) of the pelvis and a bone scan. Transgluteal tomographic cuts (5 mm thickness) are obtained by placing the patient 10 in a prone position on the CAT-scan table 12. A pad 14 is placed under the patient's pelvis to raise the gluteal area in an angulation 15. The patient is then placed in the gantry 16 by horizontal displacement (i.e., along the z axis) of the sliding top surface 18 of the table 12. The CAT-scan table 12 is fixed to the floor 20 via the table base 22.

The gantry 16 is tilted at an angle 24 which corresponds to the angulation of the patient's gluteal area (preferably between 26 and 30°). Five millimeter thick tomographic cuts are obtained throughout the prostate beginning at the seminal vesicles. The number of needles, seeds, depth and angulation are determined in a manner described in more detail below.

Prior to treatment, the patient 10 is prepped and draped in the usual manner. Intravenous sedation and local, presacral anesthesia are given by the anesthesiologist. The patient 10 undergoes routine standard monitoring by the anesthesiologist.

Transgluteal tomographic cuts (5.0 mm thickness) are obtained throughout the prostate and seminal vesicles (see above). The patient is then moved out of the gantry and underneath a stereotactic assembly 26 (see FIGS. 2–5). The stereotactic assembly 26 is adjusted to match the tilt of the gantry 24 and is positioned adjacent the gluteal region of the patient 10. A template or needle guide 29, 30 (see FIGS. 6 and 7) is mounted on the stereotactic assembly 26 and a plurality of needles are inserted into the prostate for fixation against the symphysis pubis to reduce prostate motion during subsequent needle insertion. Following fixation of the prostate the template 29, 30 is disengaged from the stereotactic assembly 26.

The patient is then moved into the original position under the gantry 16 and repeat tomographic cuts (5.0 mm thickness) are again obtained throughout the prostate. The number of needles to be used, needle depth and angulation, and the number of seeds are calculated using the grid on the CAT-scan monitor, such that the seeds are placed within and surrounding the prostate gland in a three dimensional array averaging one centimeter from center to center. The pre-calculated number of needles are inserted through the template 28 into the prostate using an aseptic technique. The patient is once again moved to the original position in the CAT-scan gantry 16 and repeat tomographic cuts are obtained. The depth of the needles may be adjusted, if necessary, at this time.

The patient is again moved under the stereotactic assembly 26 and the template is reconnected. The pre-calculated number of seeds are then implanted into the prostate using a device such as the MICK applicator (available from New York Nuclear). The needles are then incrementally extracted so as to achieve seed placement at the desired depths within the prostate. At the completion of the procedure, the needles are removed from the prostate and the patient 10 is removed from under the stereotactic assembly 26.

The floor mounted stereotactic assembly 26 (see FIGS. 2 and 3) of the present invention includes a stanchion 28 coupled to the floor 20 by a plurality of anchor studs 32. Leveling of the stanchion 28 relative to the CAT-scan table 12 is accomplished by a plurality of leveling bolts 34. An upper portion 36 of stanchion 28 comprises two vertical members 36a, 36b. A horizontal support 40 is supported by upper portion 36 in cantilevered fashion and is vertically adjustable along upper portion 36 and is lockable at any desired position therealong. Horizontal support 40 is also movable horizontally with respect to the upper portion 36 through operation of horizontal control knob 38.

A protractor 44 is supported on the distal end of horizontal support 40 and is rotatable relative to the horizontal support 40 about the longitudinal axis L thereof. In addition, a needle guide 46 is mounted on protractor 44 and is angularly adjustable relative thereto. A detailed description of the structure and operation of protractor 44 is found in applicant's U.S. Pat. Nos. 5,047,036 and 5,308,352, which disclose a stereotactic device including a protractor for use in discectomies. The disclosures of U.S. Pat. Nos. 5,047,036 and 5,308,352 are hereby incorporated by reference.

The combination of the vertical and horizontal adjustability of horizontal support 40, the rotatable adjustability of protractor 44, and the angular adjustability of needle guide 46 allow a needle placed within guide 46 to be inserted in a patient at any desired angle. Thus, precise placement of a seed within a patient is made possible through synchronization of angular and positional markings on the stereotactic device with positional information obtained from the grid on the CAT scan monitor.

Figure 4:
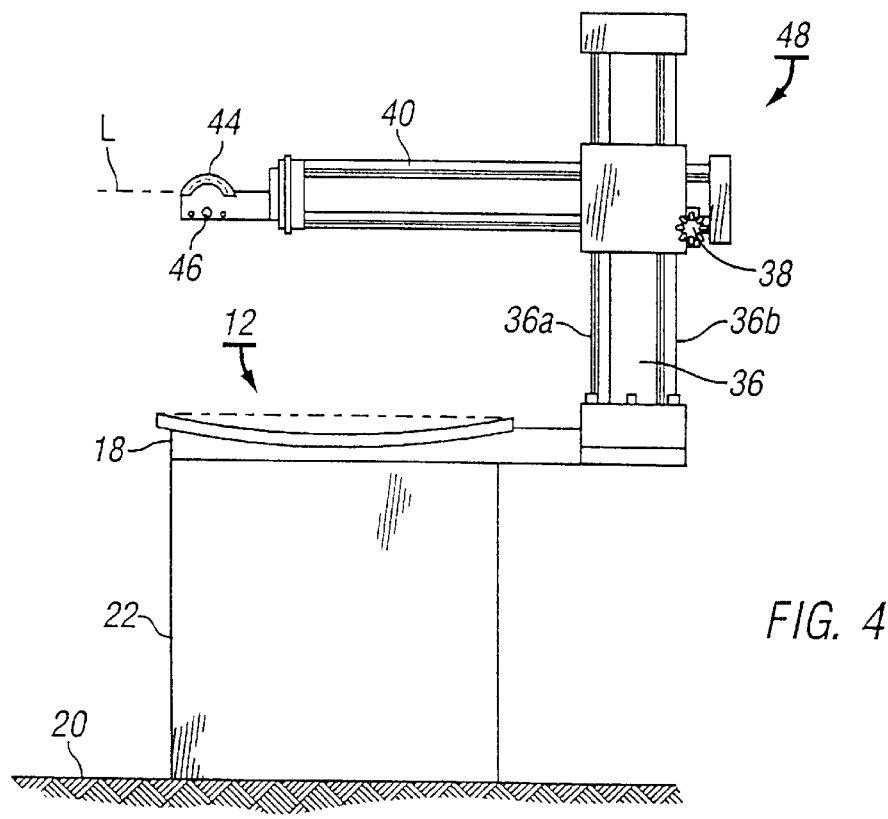
FIG. 4 is an end view of a table mounted stereotactic device assembly according to an embodiment of the invention.
Figure 8:
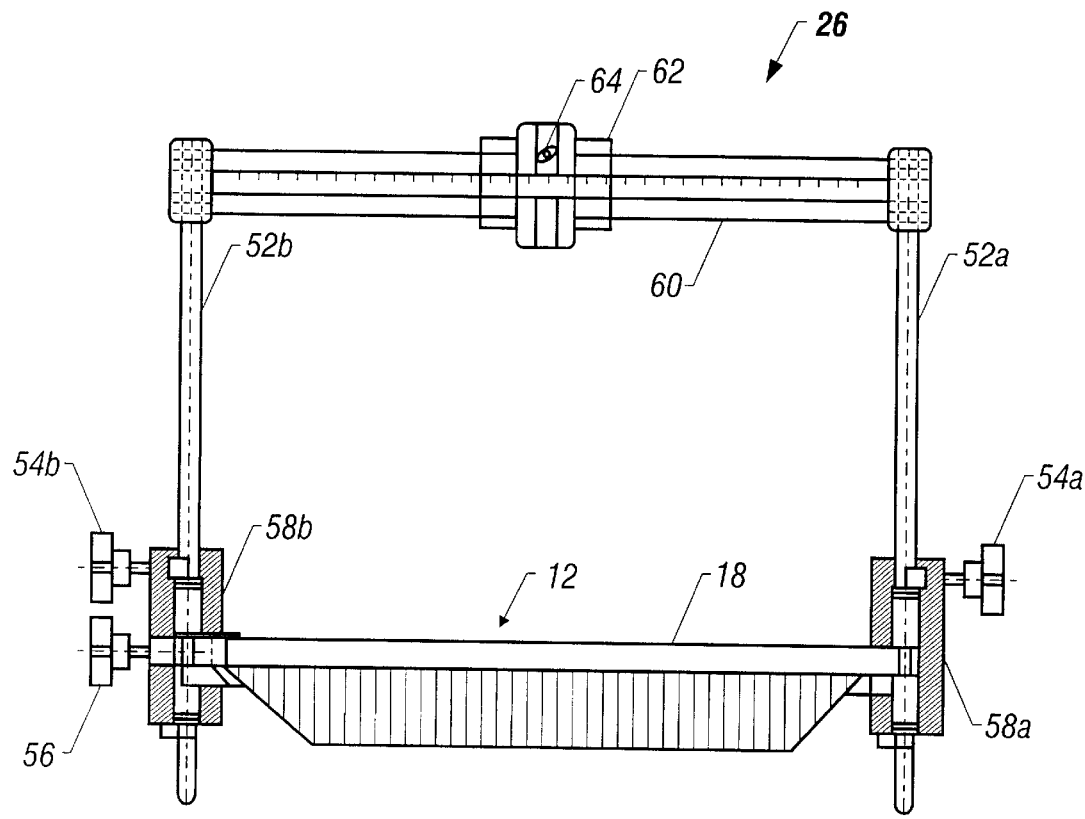
FIG. 8 is an end view of a table mounted stereotactic device assembly according to another embodiment of the invention.
Figure 9:
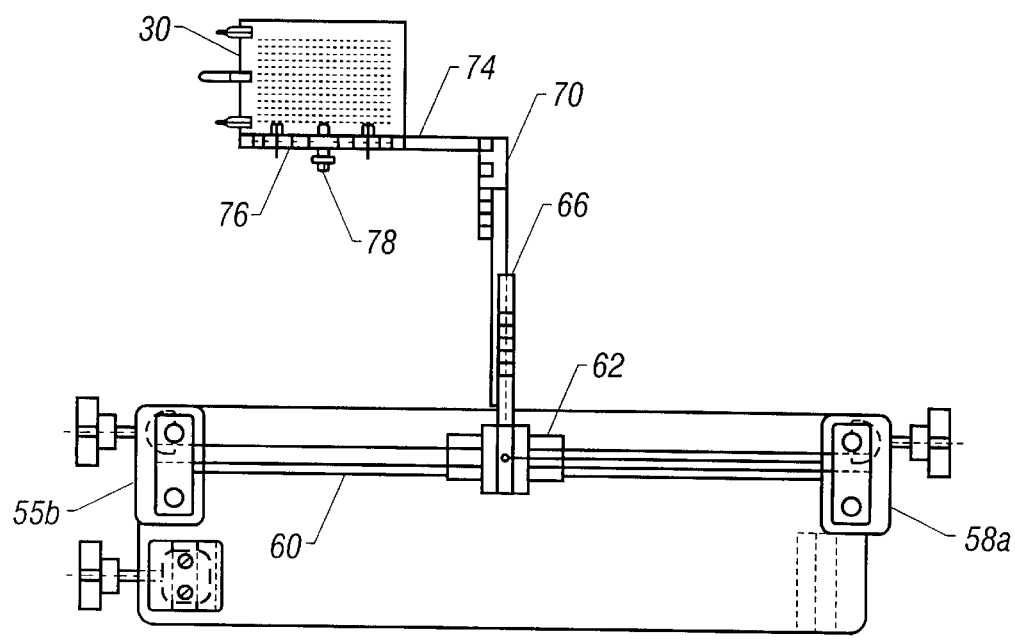
FIG. 9 is a top view of a table mounted stereotactic device assembly according to the embodiment of FIG. 8.
Figure 10:
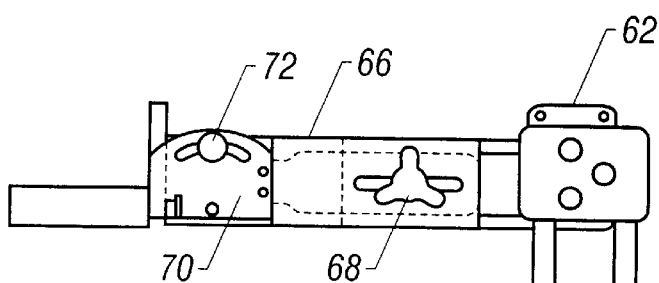
FIG. 10 is a side view of a table mounted stereotactic device assembly according to the embodiment of FIG. 8.

In another embodiment of the invention, a stereotactic assembly 48 is mounted on sliding top surface 18 of Table 12 (see FIGS. 4 and 5). Stereotactic assembly 48 omits the lower portion of stanchion 28 that was present in the floor-mounted embodiment of FIGS. 2–3. This embodiment allows execution of the brachytherapy procedure to be expedited because the stereotactic device follows the patient into the gantry and thus repeated engagement and disengagement of the stereotactic device is unnecessary.

Although a needle guide 46 having a single aperture is compatible with the method and apparatus of the present invention, in a preferred embodiment the protractor 44 is provided with a template having a plurality of apertures. In one embodiment, the template comprises a linear array 29, as shown in FIG. 6. Template 29 has, for example, apertures 50 at 0.5 centimeter intervals and is approximately 2 centimeters thick.

In another embodiment, the template comprises a two dimensional array 30 of apertures 50 spaced at, for example, 0.5 centimeter intervals along two axes. Alternatively, in another embodiment the template has a surface area of 120×80 mm, and a thickness of 20 mm. An area of 75×60 mm of the template is perforated by 2 mm (18 gauge) holes arranged in an array with 2.5 mm spacings in both directions. The template may be made of any appropriate material including, for example, Teflon® available from DuPont Corporation.

The perforations are intended to serve as guides for the needles, and the 2.5 mm spacing is selected to allow for correction of the placement of the needles as required. Use of the two-dimensional array facilitates the procedure by reducing the setup time necessary for each needle. It will be understood that the size and spacing of the perforations, as well as the size and perforated area of the template may vary according to the type of treatment and the size of target area for treatment.

Another embodiment of a stereotactic assembly in accordance with the invention is shown in FIGS. 8–11. In this embodiment, the assembly 26 is mounted to the sliding top surface 18 of table 12 by two pair 52A, 52B vertical posts. Adjustment knobs 54A, 54B allow vertical adjustment of the posts relative to the table 12. An additional knob 56 secures horizontal placement relative to the table 12. The assembly 26 is removable from the table 12 by removing posts 52A, 52B from brackets 58A, 58B.

Figure 11:
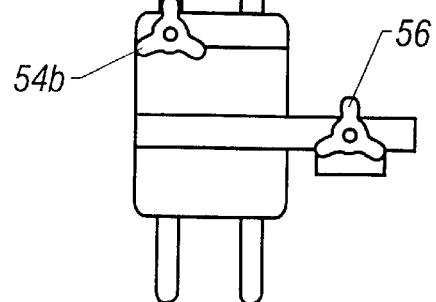
FIG. 11 is a front view of a template and protractor in accordance with an embodiment of the invention.
Figure 11:
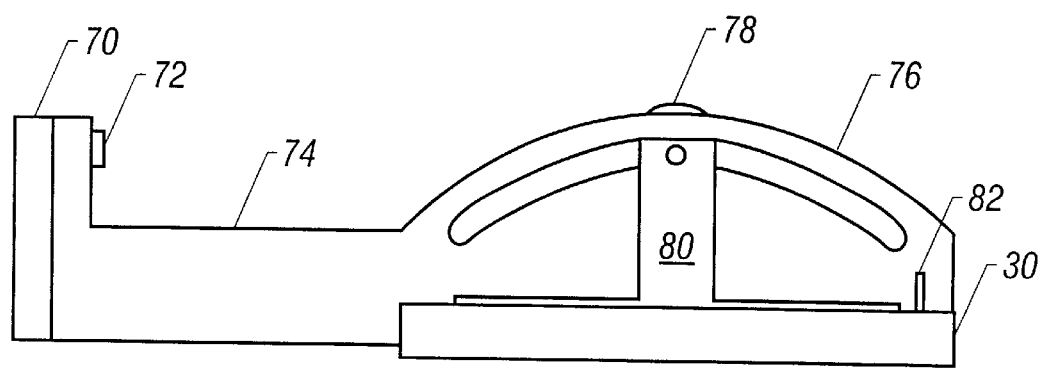

A horizontal bridge 60 is supported by posts 52A, 52B, and is graduated in millimeters. Bridge 60 carries a bracket 62 that is movable along the bridge and fixable relative thereto by means of a screw 64. Bracket 62 is provided with a horizontal telescoping arm 66, the length of which may be set by adjustment screw 68. At the distal end of arm 66 is provided a first protractor 70 having an adjustment screw 72. Protractor 70 adjustably supports a perpendicular arm 74, the distal end of which in turn supports second protractor 76. Template 30 is adjustably mounted to protractor 76, and the relative position on the protractor can be set using set screw 78. As shown in FIG. 11, template 30 is provided with a T-shaped mounting bracket 80 that allows cooperation with the set screw 78. Preferably, template 30 is provided with one or more needle holders 82 that allow a needle to be aligned with any one of the perforations in the template.

As noted above, the bridge 60 is graduated in one millimeter increments, and each of protractors 70 and 78 are graduated in one degree increments. Thus, template 30 is adjustable to a high degree of accuracy through three dimensions.

In an alternative embodiment, template 30 is provided with a 10 mm hole (not shown) at its center that is used to carry a 200 mm stainless steel piston that is graduated a spacing of 10 mm. The piston is movable through the hole in the template and its position can be fixed with a fixing nut. The length of the piston at its selected fixed position determines the distance of a needle to its point of entry.

Preferred embodiments of the invention have been disclosed and described in detail. However, the invention is not so limited, but rather is limited only by the scope of the appended claims.

What is claimed is:

1. A stereotactic apparatus for use with an imaging device in treatment of a medical condition of a patient, comprising:

an upright support member;

a span supported by and adjustable relative to the upright support member;

a protractor disposed on the span; and a needle guide supported by the protractor, the needle guide being adjustable in three dimensions to allow alignment with an image plane of the imaging device and to allow fixation of the needle guide at a desired position and angle adjacent the patient;

wherein at least a portion of the stereotactic assembly including the needle guide is movable into and out of the imaging device with the patient while the needle guide is fixed in the desired position adjacent the patient.

2. The apparatus of claim 1, wherein the needle guide comprises a template having an array of regularly spaced apertures.

3. The apparatus of claim 2, wherein said array of apertures is a two-dimensional array.

4. The apparatus of claim 1, wherein the upright support member is mounted to a moveable surface moveable into and out of the imaging device for supporting the patient, said stereotactic apparatus being movable into and out of the imaging device with the patient.

5. The apparatus of claim 1, wherein the upright support member is substantially perpendicular to the movable surface and the span is perpendicular to the upright support member.

6. The apparatus of claim 5, wherein the span is adjustable along the upright support member while the remaining perpendicular thereto.

7. The apparatus of claim 5, wherein the protractor is movable parallel to a longitudinal axis of the span.

8. A stereotactic apparatus for use with an imaging system comprising an imaging device having an aperture and a movable surface for supporting a patient that is movable into and out of the aperture, the stereotactic apparatus comprising:

a support system mounted to and movable with the movable surface; and a needle guide supported by the support system;

wherein the support system is adjustable to place the needle guide in a desired position adjacent the patient and align the needle guide with an image plane of the imaging device, and is further adjustable to permit angular adjustment of the needle guide within the image plane; and wherein the support system and the needle guide are movable into and out of the aperture of the image device with the movable surface while the needle guide is fixed in the desired position relative to the patient.

9. The apparatus of claim 8, wherein the needle guide comprises a template having an array of regularly spaced apertures.

10. The apparatus of claim 8, wherein said array of apertures is a two-dimensional array.

11. The apparatus of claim 8, wherein the support system comprises an upright support member and a span, and wherein the span supports the needle guide.

12. The apparatus of claim 11, wherein the upright support member is substantially perpendicular to the movable surface and the span is perpendicular to the upright support member.

13. The apparatus of claim 12, wherein the span is adjustable along the upright support member while the remaining perpendicular thereto.

14. The apparatus of claim 12, wherein the protractor is movable parallel to a longitudinal axis of the span.

* * * * *